US00PP21056P2

(12) United States Plant Patent
Li

(10) Patent No.: US PP21,056 P2
(45) Date of Patent: Jun. 8, 2010

(54) ***VERBENA* PLANT NAMED 'KLEVP08383'**

(50) Latin Name: *Verbena hybrida*
Varietal Denomination: KLEVP08383

(75) Inventor: Ruijun Li, North Parramata (AU)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 12/383,886

(22) Filed: Mar. 30, 2009

(51) Int. Cl.
*A01H 5/00* (2006.01)

(52) U.S. Cl. ..... Plt./308

(58) Field of Classification Search ..... Plt./308
See application file for complete search history.

*Primary Examiner*—Kent L Bell
(74) *Attorney, Agent, or Firm*—Jondle & Associates, P.C.

(57) ABSTRACT

A new cultivar of *Verbena* named 'KLEVP08383' particularly characterized by magenta inflorescences, very early flowering, a compact, semi-trailing growth habit, and good and high resistance to powdery mildew, is disclosed.

1 Drawing Sheet

Genus and species: *Verbena hybrida.*
Variety denomination: 'KLEVP08383'.

BACKGROUND OF THE NEW PLANT

The present invention comprises a new and distinct cultivar of *Verbena*, botanically known as *Verbena hybrida*, and hereinafter referred to by the cultivar name 'KLEVP08383'. 'KLEVP08383' was discovered as a seedling resulting from a cross conducted in Spring 2006 in New South Wales, Cobbitty, Australia between the proprietary female *Verbena* parent, '00.060.12' (unpatented) and the proprietary male *Verbena* parent, '00.040.33' (unpatented). A single plant selection was subsequently chosen for further evaluation and for asexual propagation.

The new cultivar was first propagated in Fall 2006 by vegetative cuttings in Stuttgart, Germany and has been asexually reproduced repeatedly by vegetative cuttings over four generations. 'KLEVP08383' has been found to retain its distinctive characteristics through successive asexual propagations.

Plant Breeder's Rights for this cultivar were applied for in Canada on Apr. 8, 2008 and in Switzerland on Aug. 15, 2008. 'KLEVP08383' has not been made publicly available more than one year prior to filing of this application.

SUMMARY OF THE INVENTION

The following are the most outstanding and distinguishing characteristics of this new cultivar when grown under normal commercial practices in a greenhouse in Stuttgart, Germany.

1. Magenta inflorescences;
2. Very early flowering;
3. A compact, semi-trailing growth habit; and
4. Good and high resistance to powdery mildew.

DESCRIPTION OF THE PHOTOGRAPH

This new *Verbena* plant is illustrated by the accompanying photograph which shows inflorescences and foliage of the plant; the colors shown are as true as can be reasonably obtained by conventional photographic procedures.

The photograph is of a plant about 4-months old and grown from rooted cuttings in open ground and grown in a greenhouse (glasshouse) in Stuttgart, Germany under natural light.

DESCRIPTION OF THE NEW CULTIVAR

The following detailed descriptions set forth the distinctive characteristics of 'KLEVP08383'. The data which define these characteristics were collected from asexual reproductions carried out in Stuttgart, Germany. The plant history was taken on 4-month old plants in open ground and grown in a glass covered greenhouse. The plants were pinched once approximately two weeks after potting. The color readings were determined under natural light. Color references are to The R.H.S. Colour Chart of The Royal Horticultural Society of London (R.H.S.) (2001).

DESCRIPTION OF THE NEW PLANT

Classification:
- *Family.*—Verbenaceae.
- *Genus and species.*—*Verbena hybrida.*
- *Common name.*—*Verbena.*

Parentage:
- *Female parent.*—The proprietary female *Verbena* plant, '00.060.12' (unpatented), having pink flowers.
- *Male parent.*—The proprietary *Verbena* plant, '00.040.33' (unpatented), having dark red flowers.

Plant:
- *Growth and branching habit.*—Compact and semi-trailing.
- *Height (from top of soil).*—25 cm.
- *Width (horizontal plant diameter).*—40 cm.
- *Time to produce a finished flowering plant.*—10 to 12 weeks.
- *Time to initiate and develop roots.*—20 days.
- *Root description.*—Smooth roots with an ovate shape.

Stems:
- *Number of branches per plant.*—Numerous, greater than 6.
- *Growth habit.*—Stems grow from the middle in a star or V-shape.
- *Length.*—Approximately 15.0 cm.

*Diameter.*—15.0 cm to 20.0 cm.
*Internode length.*—Approximately 3.5 cm.
*Color.*—RHS 135C.
*Anthocyanin.*—Absent.
*Texture and appearance.*—Shiny, ovate, and slightly pubescent.

Leaves:
*Arrangement.*—Opposite.
*Immature and mature leaf.*—Color: Upper surface: RHS 135B. Lower surface: RHS 135C.
*Length.*—2.5 cm.
*Width.*—1.5 cm.
*Shape.*—Lanceolate.
*Apex.*—Cuspidate.
*Base.*—Truncate.
*Margin.*—Serrate.
*Texture.*—Leathery.
*Venation.*—Pinnate.
*Venation color.*—Darker than RHS 135B.
*Petioles.*—Length: Less than 1.0 cm, approximately 0.1 cm. Diameter: Approximately 0.1 cm. Color: RHS 135B. Texture: Leathery.

Flower buds:
*Shape.*—Tall, cylindrical.
*Length.*—1.0 cm.
*Diameter.*—0.1 cm.
*Color* (*at tight bud*).—RHS 135C.

Inflorescence:
*Blooming habit* (*flowering season*).—Continuous.
*Lastingness of individual blooms on the plant.*—High, approximately 1 week.
*Fragrance.*—Absent.
*Inflorescence type.*—Umbel.
*Length of inflorescence.*—2.0 cm to 3.0 cm.
*Diameter of inflorescence.*—Approximately 6.0 cm.
*Number of florets per inflorescence.*—20.
*Peduncle.*—Length: Approximately 2.0 cm. Diameter: Approximately 0.1 cm. Color: RHS 61A. Texture: Leathery.

Florets:
*Form.*—Single.
*Length.*—2.0 cm.
*Diameter.*—2.0 cm.
*Color.*—Immature: Upper surface: RHS 61A. Lower surface: RHS 61D. Mature: Upper surface: RHS 61A. Lower surface: RHS 43A.
*Corolla tube length.*—0.5 cm.
*Corolla tube color.*—RHS 131B.
*Petals.*—Length of lobe: 1.0 cm. Diameter of lobe: 0.5 cm. Lobe shape: Reniform. Apex: Obtuse. Base: Acute. Margin: Sinnuate. Texture (both surfaces): Shiny.
*Pedicels.*—Length: 1.0 cm. Diameter: 0.5 cm. Color: RHS 61D. Texture and appearance: Shiny.

Calyx:
*Arrangement.*—Composed of 10 vase-shaped sepals arranged in a single row.

Sepals:
*Shape.*—Round.
*Length.*—0.5 cm.
*Diameter.*—Greater than 0.1 cm.
*Color.*—RHS 143D.
*Apex.*—Obtuse, vase-shaped.
*Base.*—Obtuse, vase-shaped.
*Margin.*—Entire.
*Texture.*—Leathery.

Reproductive organs:
*Stamens.*—Quantity: 5. Appearance: Shiny. Color: RHS 131D. Filament length: 3.0 cm. Filament diameter: 1.0 cm.
*Anther.*—Color: RHS 131C. Length: 1.0 cm. Diameter: 0.1 cm.
*Pollen.*—Amount: None, sterile.
*Pistils.*—Number: 1. Length: 1.0 cm. Diameter: Less than 0.1 cm. Stigma: Color: RHS 143D. Appearance: Shiny. Length: 0.1 cm. Diameter: Less than 0.1 cm. Style: Color: RHS 143D. Length: 0.1 cm. Diameter: Less than 0.1 cm. Appearance: Shiny.

Fruit and seed set: None observed.

Disease and insect resistance: High resistance to powdery mildew. No resistance to insects has been observed.

COMPARISON WITH PARENTAL AND COMMERCIAL CULTIVARS

'KLEVP08383' differs from the female parent, the proprietary *Verbena* '00.060.12' (unpatented) in that 'KLEVP08383' has magenta flowers, while '00.060.12' has pink flowers.

'KLEVP08383' differs from the male parent, the proprietary *Verbena* '00.040.33' (unpatented) in that 'KLEVP08383' has magenta flowers and a compact and semi-trailing habit, while '00.040.33' has dark red flowers and a semi-upright habit.

'KLEVP08383' differs from the commercial comparison variety 'Dümmen, Red Fox Empress Burgundy', article code 42109 (patent status unknown) in that 'KLEVP08383' flowers earlier than 'Dümmen, Red Fox Empress Burgundy'.

I claim:

1. A new and distinct cultivar of *Verbena* plant named 'KLEVP08383' as shown and described herein.

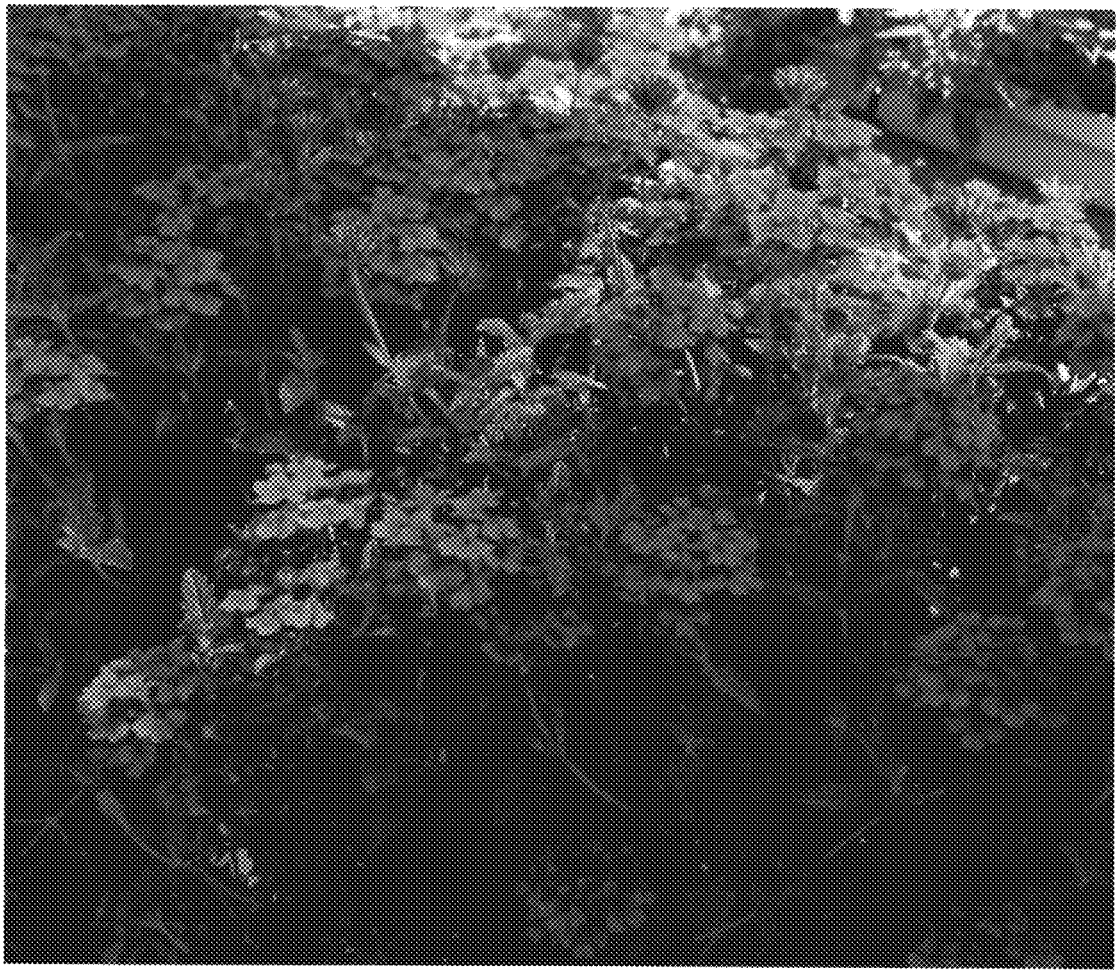

* * * * *